United States Patent
Mizuo et al.

(10) Patent No.: US 7,023,541 B2
(45) Date of Patent: Apr. 4, 2006

(54) DEVICE INSPECTING FOR DEFECT ON SEMICONDUCTOR WAFER SURFACE

(75) Inventors: Mariko Mizuo, Hyogo (JP); Toshiharu Katayama, Hyogo (JP)

(73) Assignee: Renesas Technology Corp., Tokyo (JP)

( * ) Notice: Subject to any disclaimer, the term of this patent is extended or adjusted under 35 U.S.C. 154(b) by 426 days.

(21) Appl. No.: 10/386,558

(22) Filed: Mar. 13, 2003

(65) Prior Publication Data

US 2004/0080742 A1 Apr. 29, 2004

(30) Foreign Application Priority Data

Oct. 24, 2002 (JP) .............................. 2002-309815

(51) Int. Cl.
*G01N 21/00* (2006.01)
(52) U.S. Cl. ................. 356/237.4; 356/237.5
(58) Field of Classification Search .. 356/237.1–237.5; 700/110, 103
See application file for complete search history.

(56) References Cited

U.S. PATENT DOCUMENTS

| 6,408,219 | B1 * | 6/2002 | Lamey et al. ................ 700/110 |
| 2001/0051836 | A1 * | 12/2001 | Lamey et al. ................ 700/110 |
| 2002/0027653 | A1 | 3/2002 | Shibata et al. |

FOREIGN PATENT DOCUMENTS

JP 2002-100660 4/2002

* cited by examiner

*Primary Examiner*—Michael P. Stafira
(74) *Attorney, Agent, or Firm*—Leydig, Voit & Mayer, Ltd.

(57) ABSTRACT

An inspection device inspecting for a defect of a semiconductor wafer based on an image of the wafer surface includes an imaging device obtaining image data of a wafer subjected to inspection, a storage circuit storing reference image data of the wafer, an image comparison unit comparing the image data of the wafer subjected to inspection and the reference image data using an inspection condition, an acquiring circuit acquiring wafer in process (WIP) data of the wafer subjected to inspection, and a WIP data operating unit setting the inspection condition based on the WIP data obtained.

13 Claims, 8 Drawing Sheets

DEVICE INSPECTING FOR DEFECT ON SEMICONDUCTOR WAFER SURFACE

BACKGROUND OF THE INVENTION

1. Field of the Invention

The present invention relates to an inspection for defects of a semiconductor wafer, and specifically, to an inspection for small pattern defects and foreign objects.

2. Description of the Background Art

In recent inspections for defects of semiconductor wafers, various inspection devices have been developed, with the aim of achieving higher sensitivity and broader application. Since a defect is often specific to an individual process module, sensitivity is set on defect basis. Conventionally, wafers in an identical process for an identical device have been subjected to an inspection with the same sensitivity. In other cases, such sensitivity has been adjusted by operators.

When the color of one wafer appears uneven, the inspection accuracy is degraded. In Japanese Patent Laying-Open No. 2002-100660, an inspection device with high sensitivity is disclosed. The defect inspection device described in the publication includes an optics unit acquiring the overall image of a semiconductor wafer, a display device displaying the overall image, an image processing unit dividing the image into a plurality of areas by the degree of density of the circuit pattern to be displayed on the display device, and a circuit setting a threshold value for each area for identifying potential defects.

According to the defect inspection device described in this publication, a threshold value is set for each divided area. Accordingly, a false alarm due to uneven color will not be detected, and hence an inspection with high sensitivity can be realized.

On the other hand, if the defect inspection is performed with the same inspection sensitivity, then varying wafers affected by process variations are measured with an identical inspection recipe. As a result, the inspection sensitivity will vary, making the process management difficult. Further, it is difficult to inspect even one wafer with an identical sensitivity, due to the difference in pattern density, and in thickness incurred by process variations. Still further, if operators are to adjust such sensitivity, an enormous amount of time may be required.

The defect inspection device described in this publication divides a memory/logic merged LSI (Large Scale Integrated circuit) into a memory unit, a logic unit, a peripheral circuit unit such as interface unit, and the like, corresponding to areas on a chip. For each area, the design rules of interconnections may differ, and the degree of criticality of a defect may differ depending on, for example, the type of the pattern to be layered thereon. For example, since the design rules are the smallest in the memory unit, a small foreign object or an improper pattern shape possibly becomes a critical defect. Since design rules of the pattern are relatively large and intervals between patterns are wide in the peripheral circuit unit, the size of a critical defect is large as compared to the memory unit. In such less critical peripheral circuit unit, the sensitivity of the inspection is lowered to decrease the rate of false alarm detection. Thus, a different threshold value is set for each circuit in an area, and the same areas of different LSI chips are inspected with the same sensitivity. Accordingly, the difference related to one specific LSI chip will not affect the inspection.

SUMMARY OF THE INVENTION

The object of the present invention is to provide an inspection device capable of inspecting wafer surface for defects for each wafer subjected to inspection, individually.

Another object of the present invention is to provide an inspection device capable of inspecting a wafer surface for defects with high sensitivity on an individual wafer subjected to inspection basis.

Still another object of the present invention is to provide an inspection device capable of inspecting a wafer surface for defects easily with high sensitivity on an individual wafer subjected to inspection basis.

A wafer defect inspection device according to the present invention inspects for defects based on an image of wafer surface. The inspection device includes imaging means for obtaining an image data of a wafer subjected to inspection, storage means for storing an image data of a wafer for comparison reference, comparing means for comparing the image data of the wafer subjected to inspection and the image data of the wafer for comparison reference using a pre-set inspection condition, acquiring means for acquiring a wafer in process (WIP) data of the wafer subjected to inspection, and setting means for setting the inspection condition based on the obtained WIP data.

According to the present invention, using a threshold value or the like, which is a pre-set inspection condition, inspection is performed for defects such as in the diameter of a hole. Corresponding to a variation in measured length value obtained from actual measurement of hole diameter, which is one of the WIP data, the relationship between a signal representing a defect and a signal representing a noise varies. The setting means sets a threshold value corresponding to the measured length value. The comparing means uses thus set threshold value to compare the wafer subjected to inspection and the wafer for comparison reference (a conforming item), and when they do not match, determines the wafer subjected to inspection to be a defective item. Accordingly, based on the actually measured value for each wafer, an inspection condition may be set for each wafer and thus the defect inspection may be performed with high sensitivity. As a result, a wafer defect inspection device capable of performing defect inspection with high sensitivity for each wafer subjected to inspection individually can be provided.

A wafer defect inspection device according to another aspect of the present invention includes imaging means for obtaining an image data of a wafer subjected to inspection, storage means for storing an image data of a wafer for comparison reference, comparing means for comparing the image data of the wafer subjected to inspection and the image data of the wafer for comparison reference using a pre-set inspection condition, autofocusing means for achieving focusing of the imaging means in a micro area of the wafer subjected to inspection, and setting means for calculating a height of the wafer in the micro area based on the focused position, and setting the inspection condition based on the calculated height of the wafer.

According to the present invention, using a threshold value or the like, which is a pre-set inspection condition, an inspection is performed for defects in a micro area of a wafer. Here, the imaging device achieves focusing at the micro area by the autofocusing means. In the process of focusing, the height of the wafer in the micro area can be detected. In the area with dense pattern is high in height and the area with sparse pattern is low in height. The setting means sets a threshold value corresponding to the calculated height. The comparing means uses thus set threshold value to compare the micro area of the wafer subjected to inspection and the micro area of the wafer for comparison reference (a conforming item), and when they do not match, determines the wafer subjected to inspection to be a defective item. Accordingly, the defect inspection may be performed with high sensitivity, by acquiring actually measured value of the height of each wafer in real time, and setting an inspection condition for each micro area based on the height. As a result, a wafer defect inspection device capable of performing a defect inspection with high sensitivity corresponding to each micro area of the wafer subjected to inspection individually can be provided.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
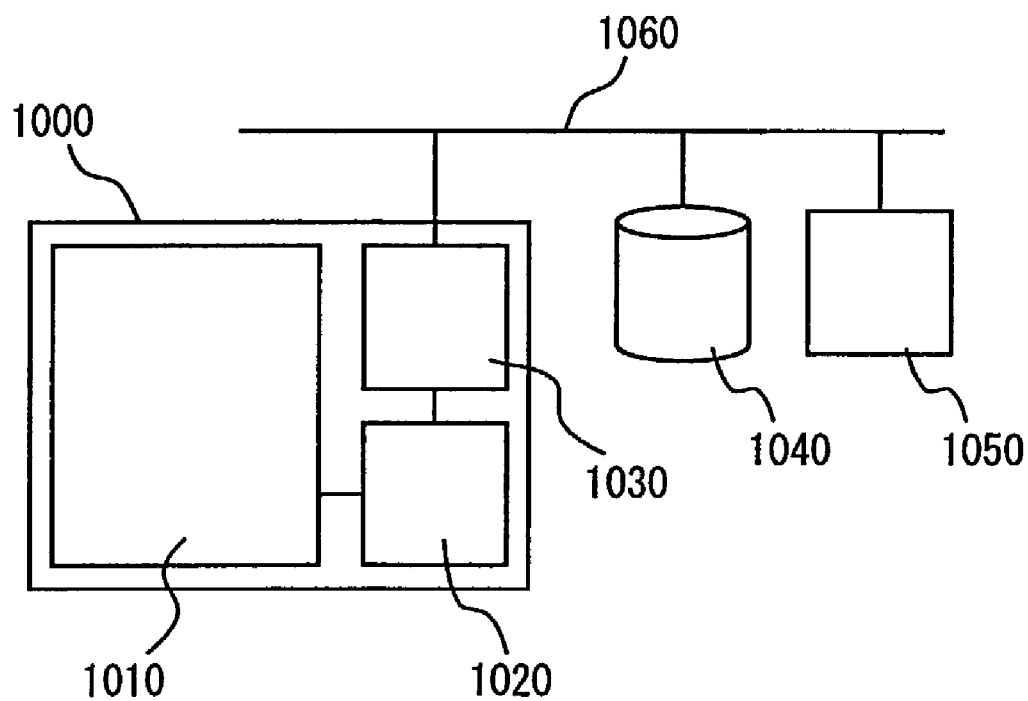
FIG. 1 shows the overall configuration of a defect inspection system according to a first embodiment of the present invention.

In the following, referring to the figures, embodiments of the present invention will be described. Throughout the description and the figures, an identical part is designated by an identical reference character, and the name and function thereof are the same. Therefore, the detailed description thereof will not be repeated.

First Embodiment

Referring to FIG. 1, the overall configuration of a defect inspection system according to a first embodiment of the present invention will be described. As shown in FIG. 1, the defect inspection system includes a defect inspection device 1000, a WIP (Wafer In Process) database 1040 connected to defect inspection device 1000 by LAN (Local Area Network) 1060, and a CIM (Computer Integrated Manufacturing) database 1050 of a factory management system. Defect inspection device 1000 includes an image comparison/detection unit 1010, a control unit 1020, a WIP data operating unit 1030.

In WIP database 1040, a measured length value, a thickness value, a registration inspection result and inspection data of prior process for each wafer are stored. In CIM database 1050, data such as a standard value of each wafer, and the order of wafer manufacturing processes are stored.

Image comparison/detection unit 1010 compares the pre-stored pattern of a conforming wafer and the pattern of a wafer subjected to defect inspection, using a threshold value calculated by WIP operating unit 1030, which will be described later, and determines a portion to be defective that significantly differs from the threshold value. WIP data operating unit 1030 reads the WIP data of the wafer subjected to defect inspection from WIP database 1040, and executes a process such as a correction of inspection sensitivity or a correction of result so as to be conformable to that WIP data. Control unit 1020 controls entire defect inspection device 1000.

It should be noted that control unit 1020 and WIP data operating unit 1030 of defect inspection device 1000 may be implemented by a computer system. Here, control unit 1020 and WIP data operating unit 1030 may be implemented by two computer systems, dividing functions for each of two, or may be implemented by one computer system with an integrated function.

Such computer system includes a computer accommodating a record medium driver, a monitor, and a keyboard. The computer includes, in addition to the record medium driver above, a CPU (Central Processing Unit), a memory and a fixed disk, connected with a bus one another. In the record medium driver, a record medium such as a FD (Flexible Disk) or a CD-ROM (Compact Disk-Read Only Memory) is loaded. Control unit 1020 and WIP data operating unit 1030 are realized by a computer hardware and software executed by CPU. Generally, such software is distributed stored in a record medium such as FD or CD-ROM, and read from the record medium by the record medium driver to be temporarily stored in the fixed disk. Thereafter, it is read from the fixed disk to the memory and executed by CPU. The hardware of the computer system itself is in common use. Therefore, one aspect of the present invention is software recorded on a record medium such as FD, CD-ROM, or fixed disk.

Figure 2:
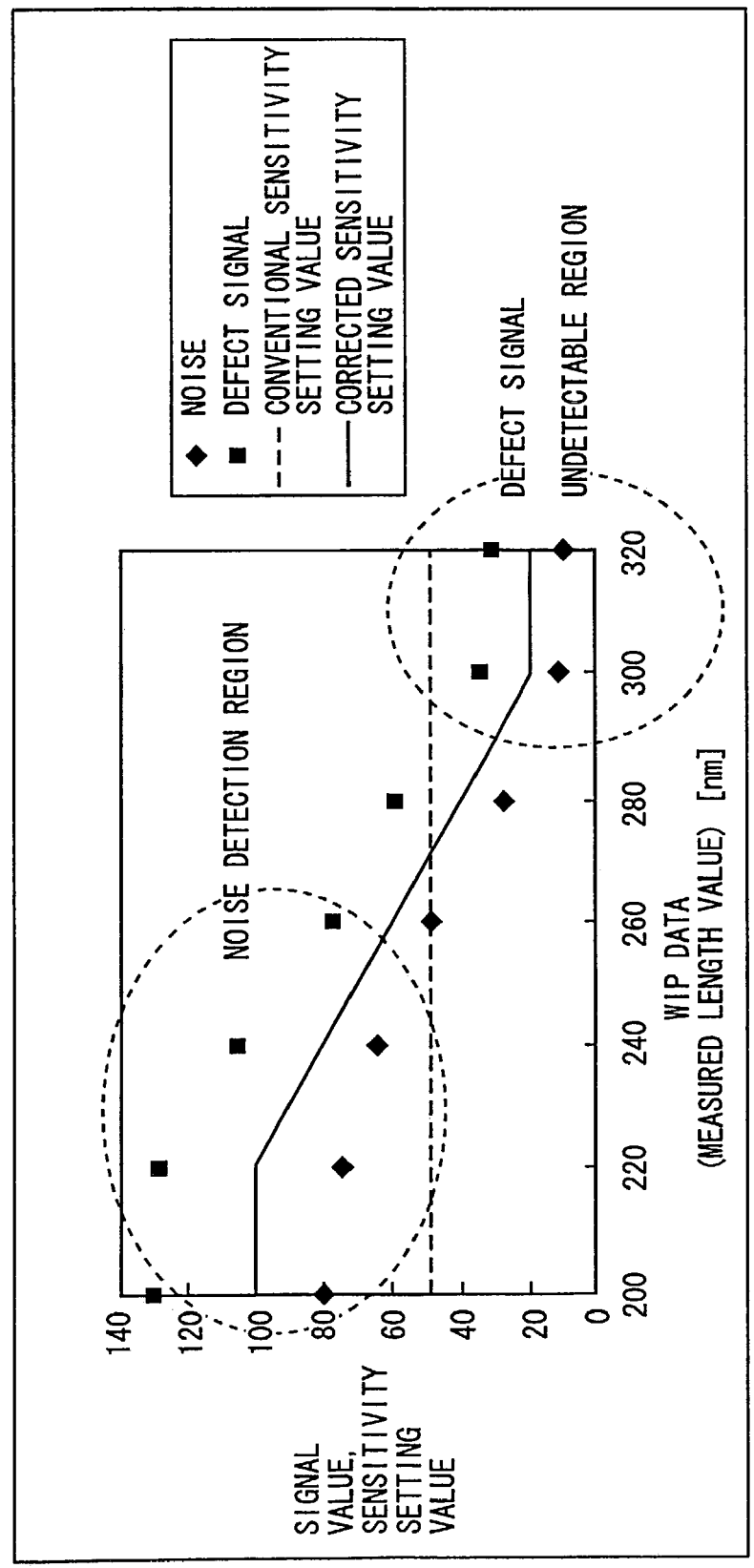
FIG. 2 is a map showing relationship between WIP data and sensitivity setting value.

Referring to FIG. 2, a map showing relationship between WIP data and sensitivity setting value will be described. The sensitivity setting value is a threshed value indicating a border between a conforming item and a defective item. As shown in FIG. 2, in a defect inspection device applying image comparing scheme, the variation in the WIP data significantly affects the inspection sensitivity. Even for wafers in an identical process, the intensity of a pattern noise signal and that of an actual defect signal are different for each WIP data (measured length value herein).

Conventionally, as shown with a straight dot line in FIG. 2, identical inspection sensitivity has been set. With such inspection sensitivity, under the effect of varying WIP data, the noise signal may be detected as a defect or the actual defect signal may not be detected in the inspection, and thus accurate inspection can not be executed.

In defect inspection system according to the present embodiment, in order to have a constant detectable minimum defect size even when measured length value varies, the inspection sensitivity (threshold value) is corrected for each measured length value. The correction sensitivity setting value for the correction is set by a user beforehand and stored as a map (hereinafter referred to as a threshold value map). In the threshold value map, the sensitivity setting value is stored, which is shown by solid line in FIG. 2. Thus, in inspection mode, WIP data operating unit 1030 reads the WIP data from WIP database 1040 to automatically correct the inspection sensitivity, and a quick defect inspection with appropriate inspection sensitivity can be achieved.

Figure 3:
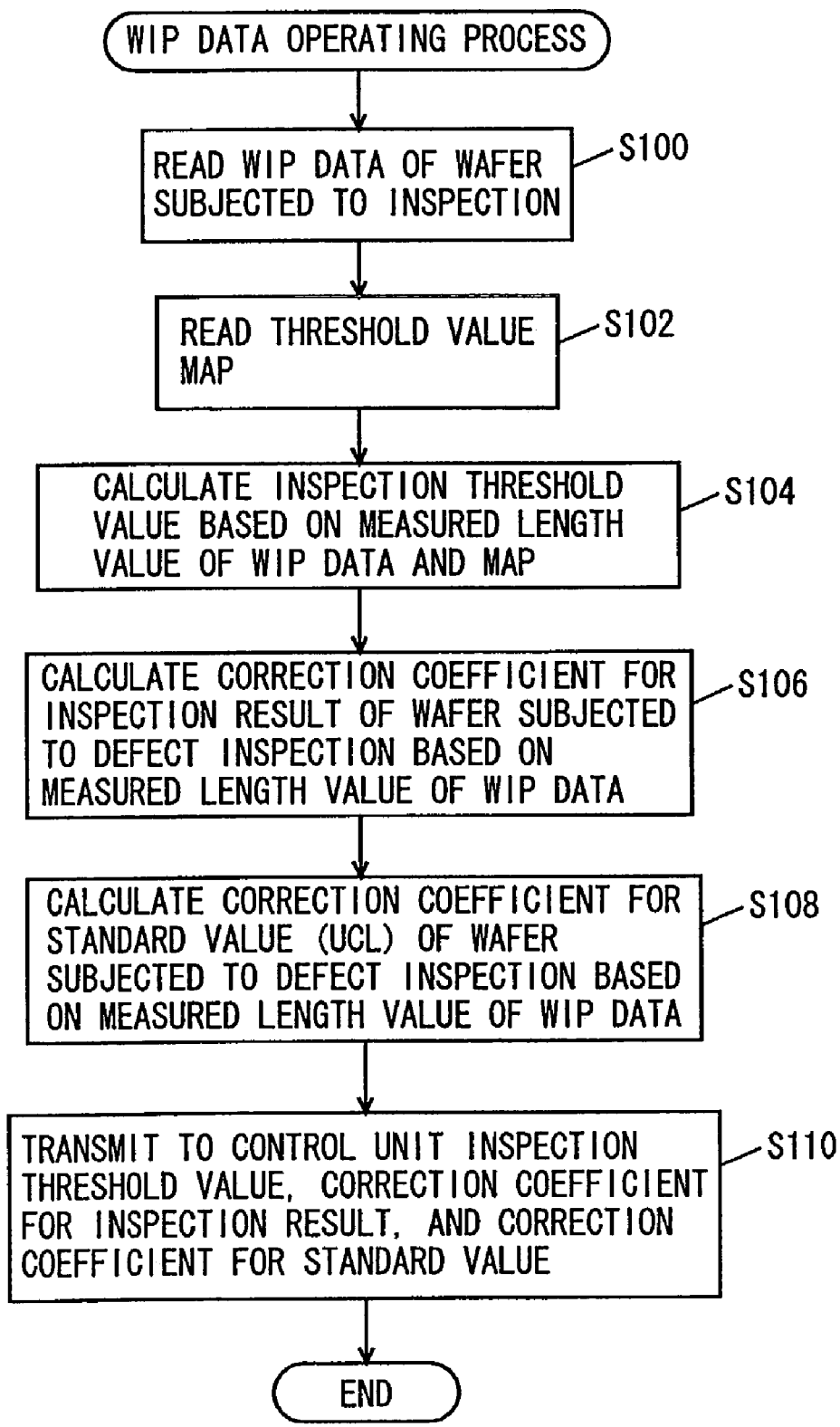
FIG. 3 is a flowchart representing processes executed by a WIP data operating unit.

Referring to FIG. 3, the procedure of processes executed by WIP data operating unit 1030 of the defect inspection system according to the present embodiment will be described.

At step (hereinafter, step will be referred to as S) 100, WIP data operating unit 130 reads WIP data of the wafer subjected to defect inspection from WIP database 1040. At S102, WIP data operating unit 1030 reads the threshold value map. At S104, WIP data operating unit 1030 calculates inspection threshold value for the wafer subjected to defect inspection, based on the measured length value of the WIP data and the threshold value map.

At S106, WIP data operating unit 1030 calculates a correction coefficient for the inspection result of the wafer subjected to defect inspection, based on the measured length value of the WIP data. Using this correction coefficient, control unit 1020 corrects the inspection result in image comparison/detection unit 1010. In other words, the inspection result is automatically corrected based on the WIP data. The defect detection number, which is the inspection result, is multiplied by the correction coefficient calculated based on the WIP data, and then output as the final defect inspection number. Thus, variation in the WIP data can be corrected. The correction coefficient for the inspection result corresponding to the WIP data is set by users beforehand.

At S108, WIP data operating unit 1030 calculates the correction coefficient for the standard value (upper control limit: UCL) of the wafer subjected to defect inspection, based on the measured length value of the WIP data. Using the correction coefficient, control unit 1020 corrects the standard value (UCL) when a statistical process of the inspection result in image comparison/detection unit 1010 is performed. In other words, the standard value (UCL) is corrected automatically based on the WIP data. By multiplying the standard value by the correction coefficient, variation in the inspection result resulted from the WIP data can be corrected. The correction coefficient for the standard value corresponding to the WIP data is set by a user beforehand.

At S110, WIP data operating unit 1030 transmits to control unit 1020 the inspection threshold value, the correction coefficient for the inspection result, and the correction coefficient for the standard value. Control unit 1020 sets the inspection threshold value as the threshold value in image comparison/detection unit 1010.

An operation of the defect inspection system according to the present embodiment, based on the structure and the flowchart above, will be described.

When a wafer subjected to inspection is set to the defect inspection system, the WIP data of the wafer subjected to inspection is read from WIP database 1040 (S100). The threshold value map (FIG. 2) is read (S102), and using the map the inspection threshold value is calculated (S104).

The correction coefficient for the inspection result of the wafer subjected to defect inspection is calculated based on the measured length value of the WIP data (S106), and the correction coefficient for the standard value (UCL) of the wafer subjected to defect inspection is calculated based on the measured length value of the WIP data. Thus calculated inspection threshold value, correction coefficient for the inspection result, and correction coefficient for the standard value are transmitted to control unit 1020. The inspection threshold value is set as the threshold value in image comparison/detection unit 1010 and thus the defect inspection is executed. The inspection result is corrected using the correction coefficient for the inspection result. The standard value for performing statistical process of the inspection result is corrected using the correction coefficient for the standard value.

As above, according to the defect inspection system according to the present invention, based on the WIP data for each wafer subjected to inspection, the inspection threshold value, the correction coefficient for the inspection result, and the correction coefficient for the standard value are calculated. Using thus calculated threshold value and correction coefficient, the defect inspection is performed, and the statistical process for the corrected inspection result is performed. As a result, based on the WIP data showing actual measured value for each wafer, the condition in inspection may be set for each wafer to perform the defect inspection with high sensitivity.

Note that, a thickness value, a registration inspection result, and an inspection result at the prior process may be used as the WIP data. The inspection result is the hardware parameter (such as alignment information, a light amount adjustment value, a focus value) obtained at the inspection in the prior process. Further, as output information, the WIP data may be added to the inspection result information. Accordingly, the output data may be used as the WIP data for a subsequent step.

Second Embodiment

In the following, a defect inspection system according to a second embodiment of the present invention will be described.

Figure 4:
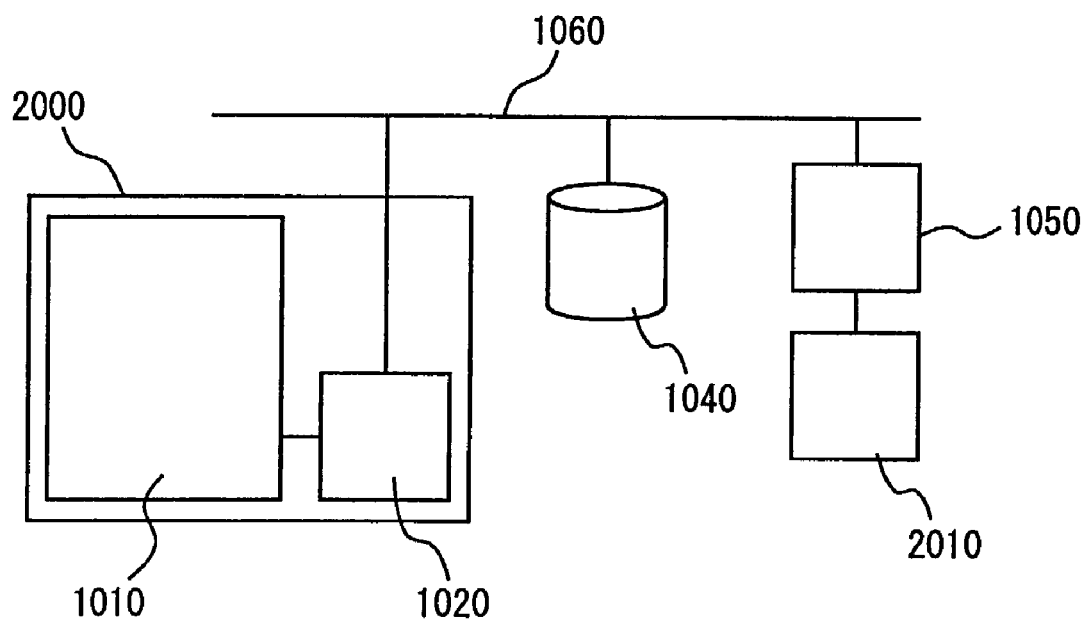
FIG. 4 shows the overall configuration of a defect inspection system according to a second embodiment of the present invention.

Referring to FIG. 4, the overall configuration of the defect inspection system according to the second embodiment of the present invention will be described. As shown in FIG. 4, the defect inspection system includes a defect inspection system 2000 in place of defect inspection system 1000 of the defect inspection system according to the first embodiment. Defect inspection system 2000 does not include WIP data operating unit 1030. Additionally, to CIM database 1050 of a factory management system, a wafer inspection device recipe operating unit 2010 is connected. The rest of the configuration is the same as the defect inspection system according to the first embodiment. Therefore, the detailed description thereof will not be repeated.

Further, wafer inspection device recipe operating unit 2010 may be implemented with a computer system similarly to control unit 1020 and WIP data operating unit 1030 above. The configuration of the computer system is the same with the defect inspection system according to the first embodiment. Therefore, the detailed description thereof will not be repeated.

Figure 5:
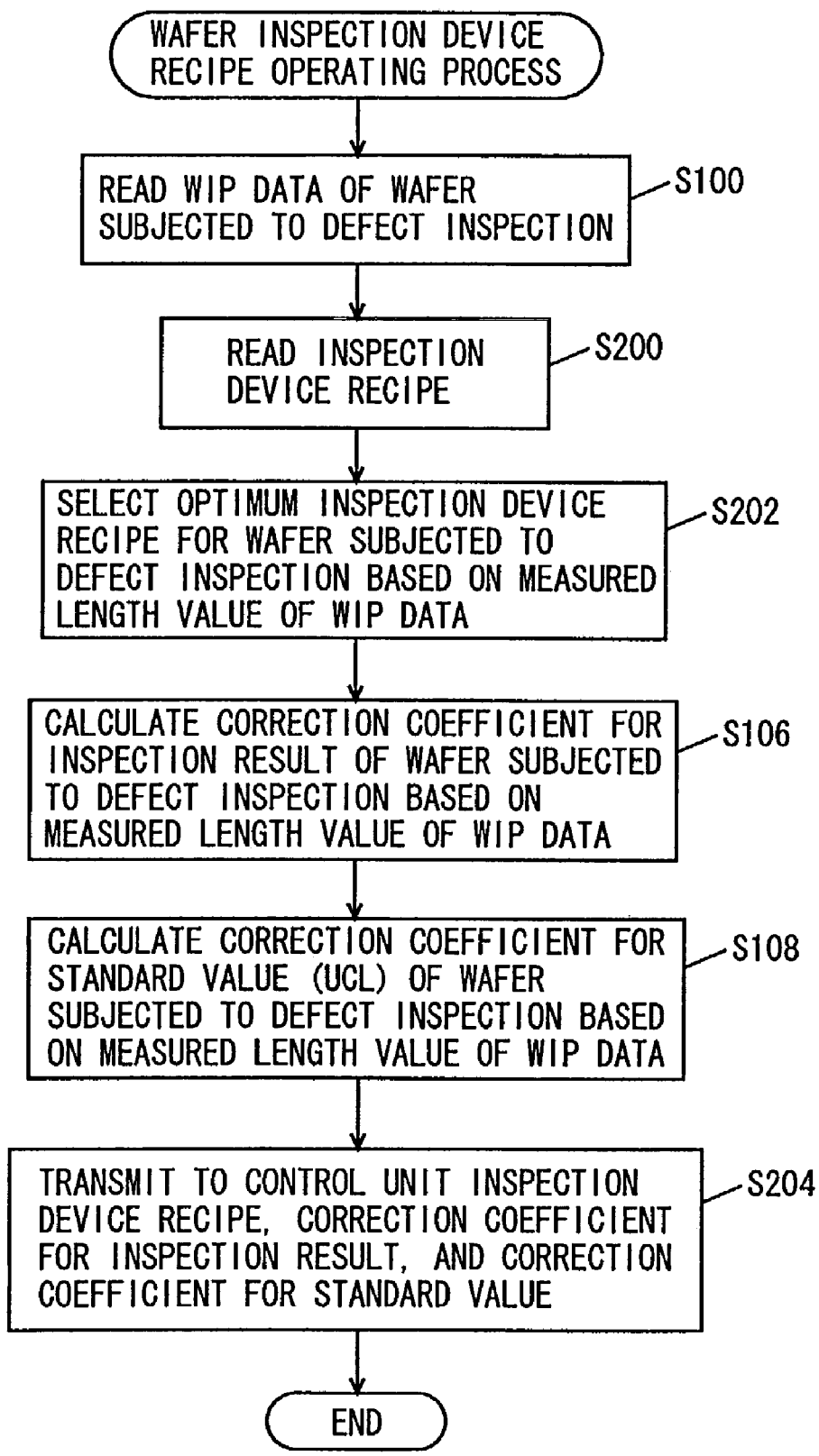
FIG. 5 is a flowchart representing processes executed by a wafer inspection device recipe operating unit.

Referring to FIG. 5, the procedure of processes executed at wafer inspection device recipe operating unit 2010 of the defect inspection system according to the present embodiment will be described. In the processes shown in FIG. 5, the same step number is given to the process that is identical to the process shown in FIG. 3. Such processes are the same. Therefore, the detailed description thereof will not be repeated.

At S200, wafer inspection device recipe operating unit 2010 reads the inspection device recipe. Here, the parameter that can be modified with the inspection device recipe is a parameter for performing defect inspection in totally different condition. For example, parameters such as inspection magnification, light amount, beam condition, type of illumination, and illumination system (bright field/dark field illumination) used in defect inspection device 2000 may be modified. As a result, even in the case where modification of the inspection threshold value is not enough for addressing problems, the defect inspection with high sensitivity may be realized by modifying the inspection device recipe.

At S202, wafer inspection device recipe operating unit 2010 selects the optimum inspection device recipe for the wafer subjected to defect inspection based on the measured length value of the WIP data. At S204, wafer inspection device recipe operating unit 2010 transmits to control unit 1020 the inspection device recipe, the correction coefficient for the inspection result, and the correction coefficient for the standard value. Control unit 1020 controls image comparison/detection unit 1010 according to the inspection recipe to perform the defect inspection.

An operation of the defect inspection system according to the present embodiment, based on the structure above and a flowchart, will be described.

When the wafer subjected to inspection is set to the defect inspection system, the WIP data of the wafer subjected to inspection is read from WIP database 1040 (S100). Then the inspection device recipe is read (S200), and from a plurality of inspection device recipes, the optimum inspection device recipe for the WIP data is selected (S202).

The correction coefficient for the inspection result of the wafer subjected to defect inspection is calculated based on the measured length value of the WIP data (S106), and the correction coefficient for the standard value (UCL) of the wafer subjected to defect inspection is calculated based on the measured length value of the WIP data. Thus calculated inspection device recipe, correction coefficient for the inspection, and correction coefficient for the standard value are transmitted to control unit 1020. According to the inspection device recipe, control unit 1020 controls image comparison/detection unit 1010 to perform the defect inspection. The inspection result is corrected using the correction coefficient for the inspection result. The standard value when performing statistical process for inspection result is corrected using the correction coefficient for the standard value.

As above, according to the defect inspection system according to the present embodiment, the wafer inspection device recipe operating unit selects a recipe including parameters in the defect inspection, based on the WIP data. The selected inspection device recipe is transmitted to defect inspection device 2000 via CIM database 1050. As a result, the optimum inspection device recipe is selected to improve the inspection accuracy.

In the present embodiment also, similar to the first embodiment, a thickness value, a registration inspection result, and an inspection result at the prior process may be used as the WIP data. The inspection result is the hardware parameter (such as alignment information, a light amount adjustment value, a focus value) obtained at the inspection in the prior process. Further, as output information, the WIP data may be added to the inspection result information. Accordingly, the output data may be used as the WIP data for a subsequent step.

Third Embodiment

In the following, a defect inspection system according to a third embodiment of the present invention will be described.

Figure 6:
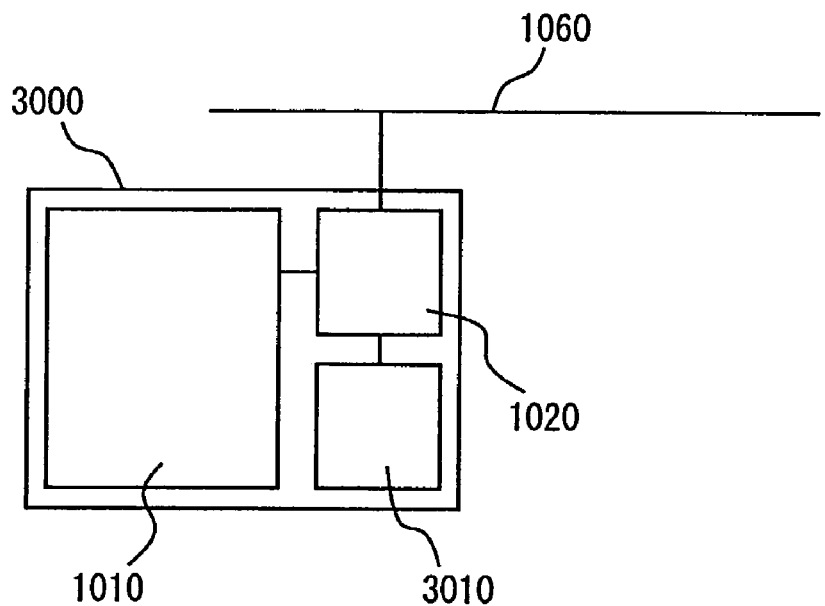
FIG. 6 shows the overall configuration of a defect inspection system according to a third embodiment of the present invention.

Referring to FIG. 6, the overall configuration of the defect inspection system according to the third embodiment of the present invention will be described. As shown in FIG. 6, the defect inspection system includes a defect inspection system 3000 in place of defect inspection system 1000 of the defect inspection system according to the first embodiment. Defect inspection system 3000 does not include WIP data operating unit 1030, and includes autofocus operating unit 3010. Auto focus operating unit 3010 is connected to control unit 1020, and sets the inspection sensitivity based on the height of the wafer detected by an autofocus operation, which automatically achieves the focus of imaging camera. This defect inspection system is different from the defect inspection system according to the first embodiment in that it does not include WIP database 1040 and CIM 1050 of the factory management system. The rest of the configuration is the same with the defect inspection system according to the first embodiment. Therefore, the detailed description thereof will not be repeated.

Auto focus operating unit 3010 can use an autofocus value obtained during the defect inspection to adjust the inspection sensitivity of the inspection condition in realtime. Auto focus operating unit 3010 obtains the autofocus value from control unit 1020 in real time, and based on the autofocus value, performs the correction of the inspection sensitivity, the correction of the result, and the like. This autofocusing is performed to the micro area on the wafer, and if the height is different, the correction of the inspection sensitivity, the correction of the result or the like is performed for each micro area in real time.

Further, autofocus operating unit 3010 may be implemented with a computer system similarly to control unit 1020 and WIP data operating unit 1030 above. The configuration of the computer system is the same with the defect inspection system according to the first embodiment. Therefore, the detailed description thereof will not be repeated.

Even on an identical wafer, microscopically, there are differences in pattern density, in height of the wafer or in thickness of the wafer, in a region such as between memory unit and logic unit or between the area on interconnection and the area off the interconnection. Such differences affect the inspection sensitivity and will result in pseudo-defect generation, sensitivity degradation, and the like. Conventionally, in order to reduce such effect, the inspection sensitivity is lowering beforehand, or a method is sought for recognizing the differences in density of a macro pattern.

Figure 7:
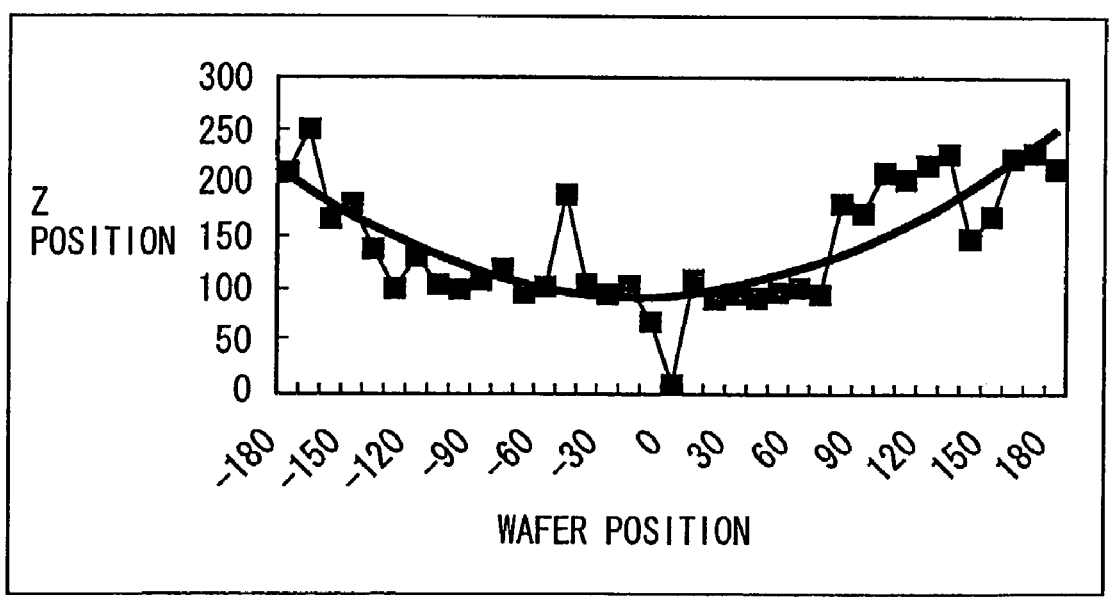
FIG. 7 shows an example of autofocusing at a micro area.
Figure 8:
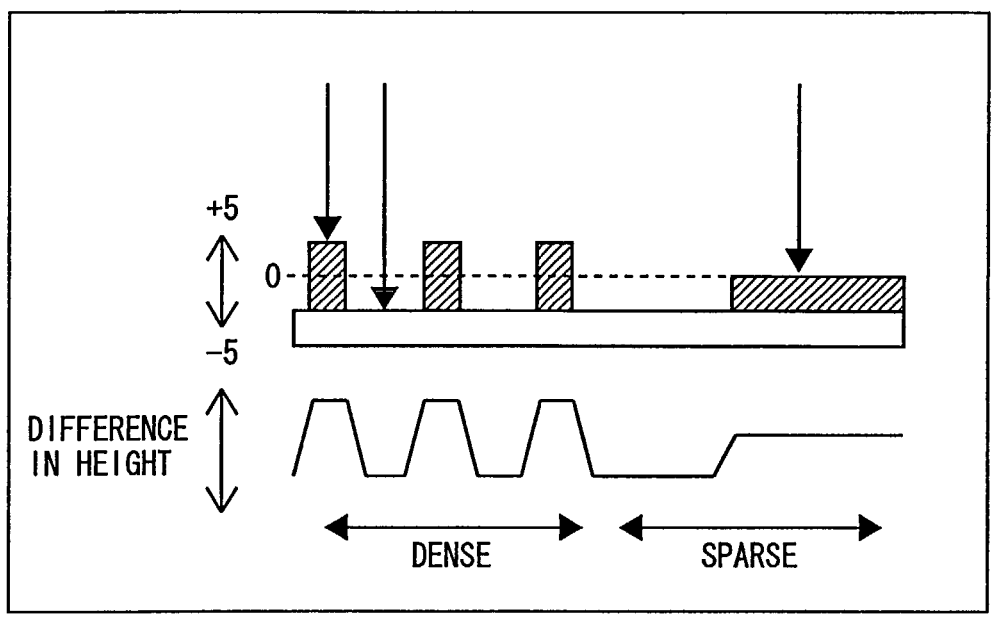
FIG. 8 is a cross sectional view of a wafer in a micro area.

The defect inspection system according to the present embodiment uses an autofocus value, obtained during the measurement of the wafer surface by defect inspection device 3000, similar to the WIP data in the first and second embodiments. In FIG. 7, height data (Z position) obtained by general autofocus (macro) operation is shown. As shown in FIG. 7, for the bow of a wafer (solid line), positions in Z direction measured through the autofocus operation vary. For example, at the wafer position 20, the Z position is low. It indicates that the autofocus position is lower in this micro area than the other area. At the wafer position around 90–150, the Z position is high., It indicates that the autofocus position is higher in this micro area than other area. In the example shown in FIG. 8, the autofocus surface of a dense pattern portion is along the dot line (Z=0), and the autofocus surface of the sparse pattern portion is Z=−2.5. In FIG. 7, the lower Z position indicates a sparse pattern, and the higher Z position indicates a dense pattern.

In defect inspection device 3000, height correction is performed using autofocus function during measurement in real time. Auto focus operating unit 3010 uses the autofocus value (height information) for micro area to determine not only the difference in pattern density but also the micro difference in height and thickness by the autofocus (height) value and the degree of fluctuation thereof, and thus execute the sensitivity correction in the micro area. Accordingly, the inspection sensitivity can rapidly be improved and optimized.

Figure 9:
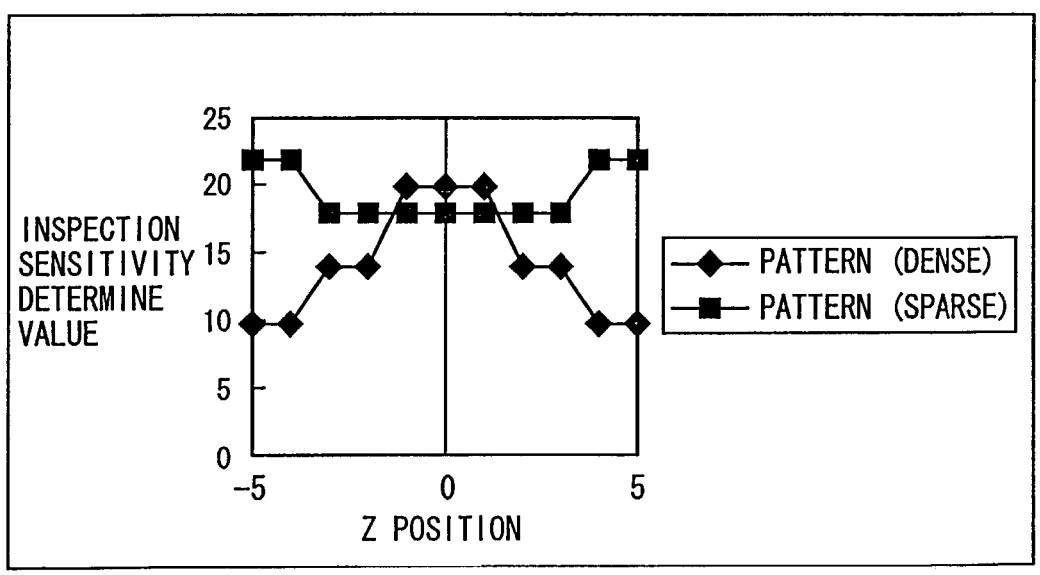
FIG. 9 is a map showing relationship between wafer height and sensitivity setting value.

The micro autofocus value (height information) obtained at control unit 1020 is transmitted to autofocus operating unit 3010 to correct the inspection sensitivity automatically. The autofocus value and the function between the degree of fluctuation of the autofocus value and the inspection sensitivity are set by a user beforehand. This is shown in FIG. 9. FIG. 9 shows the function of inspection sensitivity determining value for Z position (height information). The inspection sensitivity determining value is set respectively for two states for the sparse pattern and the dense pattern. Auto focus operating unit 3010 applies the height information to such map (hereinafter the map is referred to as an inspection sensitivity correction map) to determine the inspection sensitivity. Though in FIG. 9, the two states of the pattern (dense) and the pattern (sparse) are set, three states and above may be set.

Figure 10:
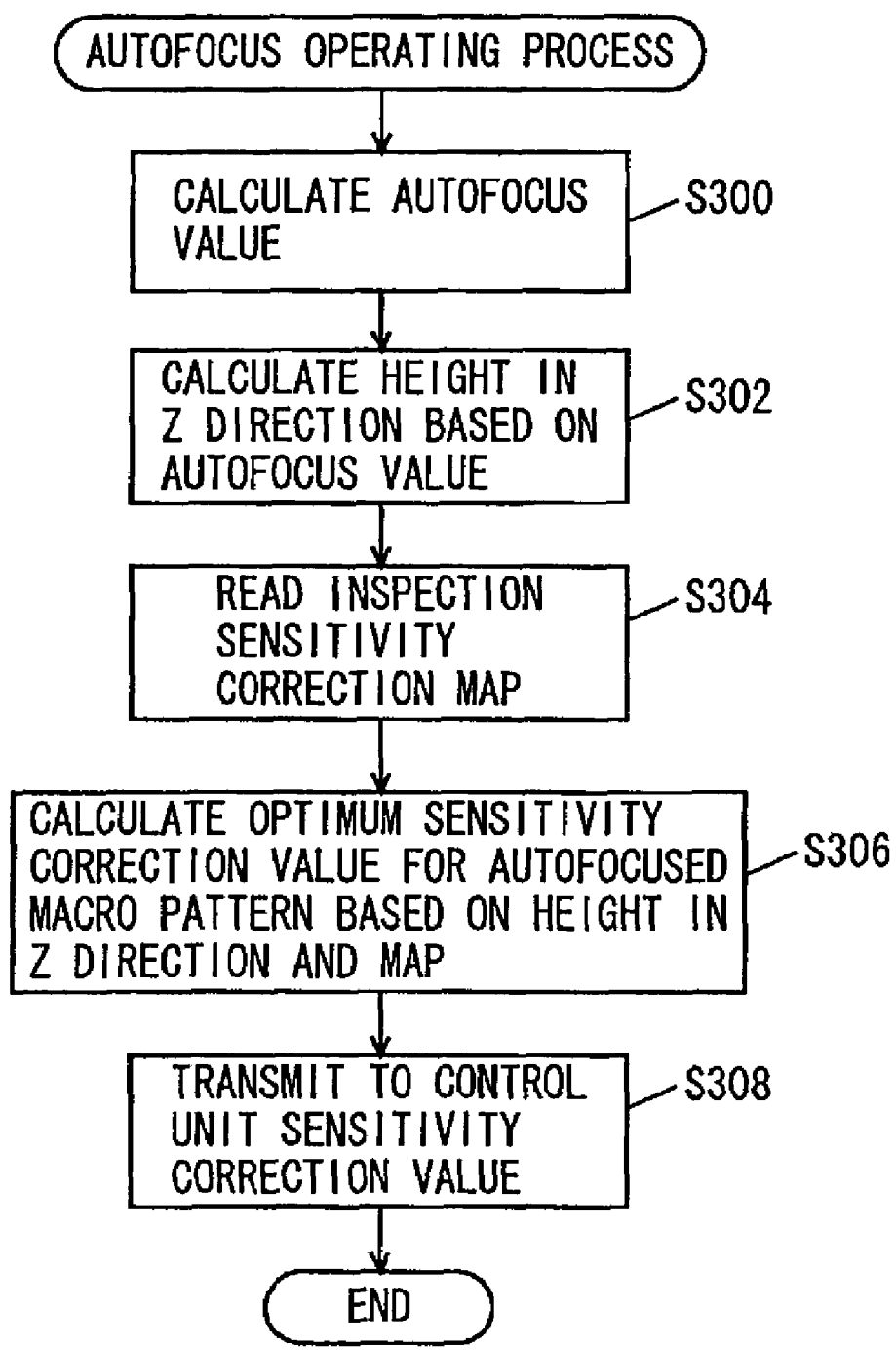
FIG. 10 is a flowchart representing processes executed by an autofocus operating unit.

Referring to FIG. 10, the procedure of the processes executed by autofocus operating unit 3010 of the defect inspection system according to the present embodiment will be described.

At S300, autofocus operating unit 3010 calculates the autofocus value based on the information received from control unit 1020. At S302, autofocus operating unit 3010 calculates Z direction height information based on the autofocus value. At S304, autofocus operating unit 3010 reads the inspection sensitivity correction map (FIG. 9). At S306, autofocus operating unit 3010 calculates the optimum sensitivity correction value for autofocused macro pattern based on the Z direction height and the map. At S308, autofocus operating unit 3010 transmits to control unit 1020 the sensitivity correction value. Control unit 1020 uses the sensitivity correction value to adjust the sensitivity in image comparison/detection unit 1010.

An operation of the detect inspection system according to the present embodiment, based on the structure above and a flowchart, will be described.

When a wafer subjected to inspection is set to the defect inspection system, the autofocus operation is executed in a micro area of the wafer subjected to inspection, and based on the information received from control unit 1020, the autofocus value is calculated by autofocus operating unit 3010 (S300). Z direction height is calculated from the autofocus value (S302), and an inspection correction map is read (S304). Based on the Z direction height and the inspection sensitivity correction map, the optimum sensitivity correction value for macro pattern is calculated (S306), and thus calculated sensitivity correction value is transmitted to control unit 1020. According to the sensitivity correction value, control unit 1020 controls image comparison/detection unit 1010 to perform the defect inspection.

As above, according to the defect inspection system according to the present embodiment, the height position of the wafer is calculated in real time by the autofocus operation of the defect inspection device in the micro area, and based on that height position and the inspection sensitivity correction map, better sensitivity is set. As a result, the height information for the micro area of the wafer is calculated in real time to adjust the inspection sensitivity, and thus the inspection accuracy can be improved.

In the present embodiment also, in addition to the inspection sensitivity, the standard value (UCL) may be adjusted based on the autofocus value as in the first embodiment. The standard value based on the autofocus value is set in real time, and the statistical process is performed to output the determination result of the defect inspection.

In the present embodiment also, the autofocus value (height information) may be added to the inspection result information as output information as in the first embodiment, or the inspection result information may be output for each autofocus value. Thus, using data only for specific condition (differences in density and height area), the standard determination or data analysis may be attained. Additionally, the standard value (UCL) may be set for each autofocus value after the defect detection.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A wafer defect inspection device inspecting for a defect based on an image of a wafer surface, comprising:
    imaging means for obtaining image data of a wafer subjected to inspection;
    storage means for storing reference image data;
    comparing means for comparing the image data of the wafer subjected to inspection and the reference image data using an inspection condition;
    acquiring means for acquiring wafer in process (WIP) data for the wafer subjected to inspection; and
    setting means for setting the inspection condition for the wafer subjected to inspection based on the WIP data acquired for the wafer subjected to inspection.

2. The wafer defect inspection device according to claim 1, wherein the inspection condition is a condition for correcting inspection sensitivity.

3. The wafer defect inspection device according to claim 2, wherein the inspection sensitivity is corrected by modifying, based on the WIP data, a threshold value determining a boundary between a conforming item and a defective item.

4. The wafer defect inspection device according to claim 1, wherein the inspection condition is an inspection recipe.

5. The wafer defect inspection device according to claim 4, wherein the inspection recipe is selected, based on the WIP data, from a plurality of inspection recipes differing in any one of inspection magnification, light amount, and beam condition.

6. The wafer defect inspection device according to claim 1, wherein the WIP data is any one of a measured length, a thickness, a registration inspection result, and inspection data of a prior process.

7. The wafer defect inspection device according to claim 1, further comprising calculating means for calculating, based on the WIP data, a correction coefficient for correcting an inspection result.

8. The wafer defect inspection device according to claim 1, further comprising calculating means for calculating, based on the WIP data, a correction coefficient for correcting a standard value used for statistical processing of inspection results.

9. The wafer defect inspection device according to claim 1, further comprising outputting means for outputting an inspection result and the WIP data.

10. A wafer defect inspection device inspecting for a defect based on an image of a wafer surface, comprising:
    imaging means for obtaining image data of a wafer subjected to inspection;
    storage means for storing reference image data;
    comparing means for comparing the image data of the wafer subjected to inspection and the reference image data using an inspection condition;
    autofocusing means for focusing of said imaging means in a micro area of the wafer subjected to inspection; and setting means for calculating height of the wafer in the micro area based on the focusing position, and setting the inspection condition based on the height calculated.

11. The wafer defect inspection device according to claim 10, wherein the inspection condition is a condition for correcting inspection sensitivity.

12. The wafer defect inspection device according to claim 10, further comprising calculating means for calculating, based on wafer in process (WIP) data, a correction coefficient for correcting a standard value used for statistical processing of inspection results.

13. The wafer defect inspection device according to claim 10, further comprising outputting means for outputting an inspection result and wafer in process (WIP) data.

* * * * *